US006571603B1

(12) United States Patent
Doleman et al.

(10) Patent No.: US 6,571,603 B1
(45) Date of Patent: Jun. 3, 2003

(54) METHOD OF RESOLVING ANALYTES IN A FLUID

(75) Inventors: Brett J. Doleman, San Francisco, CA (US); Erik J. Severin, San Marino, CA (US); Nathan S. Lewis, La Canada, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/318,900

(22) Filed: May 26, 1999

Related U.S. Application Data

(60) Provisional application No. 60/086,876, filed on May 27, 1998, and provisional application No. 60/088,804, filed on Jun. 9, 1998.

(51) Int. Cl.[7] .................... G01N 33/497; G01N 33/48
(52) U.S. Cl. .................................. 73/23.34; 702/19
(58) Field of Search ................... 73/23.34; 364/497; 359/561; 382/225; 205/787; 702/19; 706/25

(56) References Cited

U.S. PATENT DOCUMENTS

| | | | | |
|---|---|---|---|---|
| 5,078,501 A | * | 1/1992 | Hekker et al. | 359/561 |
| 5,181,259 A | * | 1/1993 | Rorvig | 382/225 |
| 5,469,369 A | | 11/1995 | Rose-Pehrsson et al. | 364/497 |
| 5,571,401 A | * | 11/1996 | Lewis et al. | 205/787 |
| 5,619,428 A | * | 4/1997 | Lee et al. | 702/19 |
| 5,654,497 A | | 8/1997 | Hoffheins et al. | 73/23.2 |
| 5,926,804 A | * | 7/1999 | Tufts et al. | 706/25 |

OTHER PUBLICATIONS

Polikar et al, Nonlinear Cluster Transformations for Increasing Pattern Separability, Proceedings of International Conference on Nueral Networks, Part vol. 6, p. 4006–11 vol. 6, IEEE, Jul. 1999.*

Gutierrez Osuna et al, Method for Evaluating Data Preprocessing Techniques for Odor Classification, IEEE Transactions on systems, Man, and Cybernetics, Part B: Cybernetics, 1999, 29(5) 626–632.*
Odorico, Neural 2—A program for neural net and statistical pattern recognition, Computer Physics Communications (1996), 96(2&3), 314–330*
Sendecor et al, Statistical Methods, Iowa State University Press, Ames, Iowa, 1989.*
Doleman et al, *Anal. Chem.*, 70:4177–4190 (1998).
Poston et al., *Pattern Recognition*, 31(7):881–888 (1998).
Lonergan et al., *Chem. Mater.*, 8:2298–2312 (1998).
Horner, *Technisches Messen TM*, 62(4):186–172 (1995).
Mallet et al., *Chemometrics and Intelligent Laboratory Systems*, 35:167–173 (1996).
Freund et al, *Proc. Natl. Acad. Sci. USA*, 92:2652–2656 (1995).

* cited by examiner

*Primary Examiner*—Daniel S. Larkin
*Assistant Examiner*—Jay L Politzer
(74) *Attorney, Agent, or Firm*—Townsend & Townsend & Crew LLP

(57) ABSTRACT

A statistical metric, based on the magnitude and standard deviations along linear projections of clustered array response data, is utilized to facilitate an evaluation of the performance of detector arrays in various vapor classification tasks. This approach allows quantification of the ability of arrays of different types including carbon black-insulating polymer composite chemiresistor sensors, tin oxide sensors and bulk conducting organic polymer sensors to distinguish between analytes. The evaluation of questions such as the optimal number of detectors required for a specific task, whether improved performance is obtained by increasing the number of detectors in a detector array, and how to assess statistically the diversity of a collection of detectors in order to understand more fully which properties are underrepresented in a particular set of array elements, are addressed.

16 Claims, 11 Drawing Sheets

| | acetone | acetonitrile | anisole | benzene | butylamine | chloroform | cyclohexane | dichloromethane | ethanol | ethyl acetate | isopropanol | methanol | n-heptane | n-pentane | tetrahydrofuran | toluene | triethylamine | α,α,α-trifluorotoluene |
|---|---|---|---|---|---|---|---|---|---|---|---|---|---|---|---|---|---|---|
| 1,2-dimethoxyethane | 121 | 194 | 71 | 49 | 58 | 95 | 287 | 130 | 135 | 164 | 184 | 230 | 156 | 354 | 130 | 179 | 73 | 119 |
| acetone | | 51 | 102 | 98 | 44 | 106 | 88 | 42 | 58 | 93 | 107 | 41 | 95 | 172 | 42 | 227 | 138 | 198 |
| acetonitrile | | | 154 | 173 | 54 | 153 | 152 | 73 | 58 | 171 | 207 | 75 | 119 | 135 | 88 | 317 | 174 | 200 |
| anisole | | | | 106 | 23 | 178 | 146 | 130 | 107 | 126 | 131 | 129 | 140 | 182 | 145 | 59 | 78 | 60 |
| benzene | | | | | 52 | 65 | 177 | 132 | 117 | 58 | 140 | 202 | 112 | 195 | 102 | 229 | 47 | 82 |
| butylamine | | | | | | 55 | 63 | 53 | 48 | 36 | 82 | 86 | 76 | 54 | 48 | 41 | 57 | 65 |
| chloroform | | | | | | | 123 | 102 | 122 | 133 | 126 | 204 | 92 | 231 | 159 | 303 | 146 | 180 |
| cyclohexane | | | | | | | | 109 | 103 | 180 | 108 | 151 | 202 | 152 | 153 | 528 | 132 | 312 |
| dichloromethane | | | | | | | | | 57 | 121 | 60 | 72 | 132 | 54 | 63 | 489 | 246 | 384 |
| ethanol | | | | | | | | | | 119 | 102 | 57 | 77 | 77 | 51 | 279 | 125 | 137 |
| ethyl acetate | | | | | | | | | | | 88 | 201 | 123 | 181 | 59 | 253 | 122 | 151 |
| isopropanol | | | | | | | | | | | | 135 | 161 | 119 | 73 | 313 | 218 | 206 |
| methanol | | | | | | | | | | | | | 107 | 58 | 87 | 401 | 308 | 260 |
| n-heptane | | | | | | | | | | | | | | 177 | 161 | 380 | 156 | 90 |
| n-pentane | | | | | | | | | | | | | | | 217 | 556 | 171 | 343 |
| tetrahydrofuran | | | | | | | | | | | | | | | | 359 | 93 | 178 |
| toluene | | | | | | | | | | | | | | | | | 246 | 180 |
| triethylamine | | | | | | | | | | | | | | | | | | 168 |

FIG. 4A

14 Carbon Black-Polymer Composite Detectors

| | acetone | acetonitrile | anisole | benzene | butylamine | chloroform | cyclohexane | dichloromethane | ethanol | ethyl acetate | isopropanol | methanol | n-heptane | n-pentane | tetrahydrofuran | toluene | triethylamine | α,α,α-trifluorotoluene |
|---|---|---|---|---|---|---|---|---|---|---|---|---|---|---|---|---|---|---|
| 1,2-dimethoxyethane | 18 | 48 | 102 | 10 | 7.3 | 120 | 44 | 106 | 7.3 | 35 | 18 | 15 | 5.5 | 64 | 33 | 26 | 7.2 | 22 |
| acetone | | 36 | 59 | 6.5 | 11 | 50 | 10 | 47 | 8.1 | 15 | 11 | 12 | 10 | 11 | 17 | 27 | 16 | 19 |
| acetonitrile | | | 57 | 7.3 | 29 | 103 | 13 | 94 | 49 | 14 | 26 | 21 | 21 | 26 | 23 | 15 | 33 | 49 |
| anisole | | | | 23 | 45 | 53 | 37 | 53 | 67 | 54 | 57 | 48 | 43 | 56 | 41 | 54 | 66 | 51 |
| benzene | | | | | 13 | 9.7 | 7.0 | 12 | 7.8 | 8.6 | 8.3 | 6.9 | 4.9 | 5.2 | 5.1 | 11 | 14 | 9.7 |
| butylamine | | | | | | 37 | 36 | 36 | 10 | 26 | 16 | 12 | 9.1 | 31 | 22 | 22 | 3.8 | 30 |
| chloroform | | | | | | | 37 | 20 | 24 | 34 | 47 | 44 | 27 | 38 | 16 | 149 | 38 | 7.9 |
| cyclohexane | | | | | | | | 25 | 10 | 13 | 22 | 19 | 12 | 6.6 | 8.8 | 19 | 24 | 8.9 |
| dichloromethane | | | | | | | | | 25 | 32 | 48 | 35 | 27 | 25 | 20 | 116 | 36 | 4.9 |
| ethanol | | | | | | | | | | 16 | 12 | 11 | 7.2 | 20 | 20 | 34 | 11 | 12 |
| ethyl acetate | | | | | | | | | | | 13 | 14 | 19 | 17 | 12 | 21 | 21 | 17 |
| isopropanol | | | | | | | | | | | | 15 | 7.7 | 53 | 25 | 16 | 16 | 19 |
| methanol | | | | | | | | | | | | | 11 | 14 | 11 | 16 | 20 | 26 |
| n-heptane | | | | | | | | | | | | | | 23 | 25 | 9.1 | 12 | 28 |
| n-pentane | | | | | | | | | | | | | | | 14 | 29 | 27 | 16 |
| tetrahydrofuran | | | | | | | | | | | | | | | | 17 | 26 | 9.6 |
| toluene | | | | | | | | | | | | | | | | | 26 | 48 |
| triethylamine | | | | | | | | | | | | | | | | | | 23 |

8 Tin Oxide Detectors

FIG. 4B

| | acetone | acetonitrile | anisole | benzene | butylamine | chloroform | cyclohexane | dichloromethane | ethanol | ethyl acetate | isopropanol | methanol | n-heptane | n-pentane | tetrahydrofuran | toluene | triethylamine | α,α,α-trifluorotoluene |
|---|---|---|---|---|---|---|---|---|---|---|---|---|---|---|---|---|---|---|
| 1,2-dimethoxyethane | 5.7 | 24 | 9.7 | 7.3 | 10 | 9.5 | 8.7 | 6.5 | 46 | 5.5 | 25 | 29 | 9.8 | 11 | 9.5 | 7.7 | 21 | 8.4 |
| acetone | | 22 | 15 | 14 | 11 | 16 | 19 | 6.7 | 64 | 12 | 35 | 29 | 20 | 18 | 14 | 10 | 19 | 8.7 |
| acetonitrile | | | 36 | 35 | 23 | 45 | 32 | 23 | 54 | 27 | 36 | 28 | 41 | 39 | 45 | 31 | 43 | 34 |
| anisole | | | | 3.1 | 12 | 4.4 | 7.1 | 12 | 26 | 6.9 | 17 | 42 | 8.5 | 9.5 | 14 | 3.5 | 9.9 | 5.0 |
| benzene | | | | | 13 | 2.7 | 2.8 | 4.3 | 18 | 5.0 | 7.9 | 31 | 3.3 | 4.4 | 8.8 | 3.5 | 9.8 | 2.0 |
| butylamine | | | | | | 12 | 14 | 11 | 35 | 17 | 12 | 40 | 12 | 11 | 11 | 12 | 18 | 12 |
| chloroform | | | | | | | 6.1 | 6.8 | 37 | 6.2 | 8.4 | 35 | 7.3 | 12 | 10 | 3.4 | 10 | 5.1 |
| cyclohexane | | | | | | | | 3.5 | 66 | 7.5 | 22 | 27 | 1.6 | 4.3 | 9.8 | 4.5 | 12 | 2.6 |
| dichloromethane | | | | | | | | | 57 | 4.0 | 15 | 31 | 4.0 | 5.7 | 4.8 | 5.2 | 14 | 3.5 |
| ethanol | | | | | | | | | | 62 | 78 | 55 | 49 | 46 | 42 | 16 | 49 | 24 |
| ethyl acetate | | | | | | | | | | | 20 | 29 | 11 | 9.4 | 11 | 4.9 | 14 | 5.2 |
| isopropanol | | | | | | | | | | | | 39 | 12 | 21 | 10 | 8.0 | 39 | 6.4 |
| methanol | | | | | | | | | | | | | 35 | 41 | 38 | 30 | 38 | 34 |
| n-heptane | | | | | | | | | | | | | | 4.4 | 5.5 | 4.7 | 9.2 | 1.4 |
| n-pentane | | | | | | | | | | | | | | | 9.3 | 5.2 | 15 | 4.2 |
| tetrahydrofuran | | | | | | | | | | | | | | | | 4.9 | 16 | 5.5 |
| toluene | | | | | | | | | | | | | | | | | 13 | 4.4 |
| triethylamine | | | | | | | | | | | | | | | | | | 9.7 |

12 Bulk Conducting Organic Polymer Detectors

FIG. 4C

| | 1,2-dimethoxyethane | acetone | acetonitrile | anisole | benzene | butylamine | chloroform | cyclohexane | dichloromethane | ethanol | ethyl acetate | isopropanol | methanol | n-heptane | n-pentane | tetrahydrofuran | toluene | triethylamine |
|---|---|---|---|---|---|---|---|---|---|---|---|---|---|---|---|---|---|---|
| acetone | 59 | | | | | | | | | | | | | | | | | |
| acetonitrile | 107 | 30 | | | | | | | | | | | | | | | | |
| anisole | 76 | 74 | 154 | | | | | | | | | | | | | | | |
| benzene | 61 | 88 | 176 | 40 | | | | | | | | | | | | | | |
| butylamine | 59 | 29 | 70 | 23 | 54 | | | | | | | | | | | | | |
| chloroform | 110 | 86 | 145 | 134 | 92 | 55 | | | | | | | | | | | | |
| cyclohexane | 120 | 103 | 167 | 91 | 100 | 75 | 74 | | | | | | | | | | | |
| dichloromethane | 41 | 56 | 81 | 117 | 88 | 65 | 89 | 111 | | | | | | | | | | |
| ethanol | 68 | 47 | 63 | 90 | 115 | 37 | 97 | 159 | 63 | | | | | | | | | |
| ethyl acetate | 103 | 59 | 107 | 106 | 84 | 35 | 139 | 120 | 48 | 55 | | | | | | | | |
| isopropanol | 58 | 77 | 208 | 88 | 144 | 67 | 95 | 107 | 59 | 90 | 124 | | | | | | | |
| methanol | 61 | 32 | 40 | 126 | 168 | 54 | 166 | 151 | 70 | 30 | 149 | 89 | | | | | | |
| n-heptane | 157 | 93 | 133 | 128 | 113 | 116 | 154 | 85 | 110 | 79 | 185 | 181 | 74 | | | | | |
| n-pentane | 129 | 64 | 99 | 100 | 99 | 21 | 89 | 107 | 45 | 60 | 50 | 55 | 54 | 98 | | | | |
| tetrahydrofuran | 74 | 58 | 91 | 119 | 136 | 31 | 146 | 107 | 42 | 50 | 42 | 84 | 71 | 221 | 56 | | | |
| toluene | 111 | 82 | 225 | 48 | 31 | 31 | 118 | 141 | 229 | 189 | 157 | 123 | 187 | 187 | 119 | 184 | | |
| triethylamine | 97 | 105 | 171 | 102 | 51 | 74 | 142 | 40 | 197 | 112 | 158 | 203 | 240 | 203 | 70 | 112 | 82 | |
| α,α,α-trifluorotoluene | 138 | 148 | 182 | 58 | 43 | 77 | 156 | 71 | 256 | 111 | 143 | 141 | 149 | 82 | 109 | 149 | 27 | 96 |

FIG. 5

| Sensor # | Polymer |
|---|---|
| 1 | poly(4-vinyl phenol) |
| 2 | poly(vinyl chloride-co-vinyl acetate), 10% vinyl acetate |
| 3 | poly(N-vinylpyrrolidone) |
| 4 | poly(vinyl acetate) |
| 5 | poly(methyl vinyl ether-co-maleic anhydride) |
| 6 | poly(carbonate bispenol A) |
| 7 | poly(styrene) |
| 8 | poly(sulfone) |
| 9 | poly(methyl methacrylate |
| 10 | poly(vinylidene chloride-co-acrylonitrile), 80% vinylidene chloride |
| 11 | poly(caprolactone) |
| 12 | poly(ethylene-co-vinyl acetate), 82% ethylene |
| 13 | poly(ethylene oxide) |
| 14 | poly(9-vinylcarbazole) |

FIG. 6

| | | carbon black-polymer | conducting ploymer | tin oxide |
|---|---|---|---|---|
| carbon black-polymer | average rf<br>worst rf | 9.7<br>0.91 | 9.8<br>1.8 | 9.0<br>0.88 |
| conducting ploymer | average rf<br>worst rf | | 5.2<br>0.30 | 7.2<br>0.62 |
| tin oxide | average rf<br>worst rf | | | 5.8<br>0.46 |
| carbon black-polymer, conducting polymer, and tin oxide arrays | | | average rf:<br>worst rf: | 9.4<br>0.95 |

FIG. 10

METHOD OF RESOLVING ANALYTES IN A FLUID

RELATED CASES

The present patent application claims priority from U.S. Provisional Application No. 60/086,876, filed May 27, 1998 and from U.S. Provisional Application No. 60/088,804, filed Jun. 9, 1998.

STATEMENT AS TO RIGHTS TO INVENTIONS MADE UNDER FEDERALLY SPONSORED RESEARCH AND DEVELOPMENT

The United States Government may have certain rights to the present invention pursuant to Grant No. DAAG55-97-1-0187 awarded by the U.S. Army and Grant No. DAAK60-97-K-9503 awarded by the U.S. Navy.

BACKGROUND OF THE INVENTION

The present invention is related to the electrochemical sensing of analytes in a medium or a vacuum, such as odors, smells, vapors and the like in air, and in particular, to methods of determining or resolving such analytes once detected.

There has been considerable interest in developing devices for the general detection of analytes in a fluid, vacuum, air, or other medium. A specific instance of an analyte detector is a device for sensing smells or odors (i.e., analytes in air). It is well recognized that some animals, such as dogs, have a much keener sense of smell than human beings. Because of the acuity of their noses, dogs have been utilized for many tasks including, for example, the detection of bombs, mines, drugs, poison gases, and illegal contraband; dogs also aid in the search and rescue of humans. Devices for sensing smell would be useful for the applications where animals are traditionally used, as well as for a multitude of uses where animals are impractical or inappropriate.

Moreover, devices for the general detection of analytes have potentially many more applications than devices for detecting only smells and odors. For example, the uses for devices for analyte detection include the detection of chemical leaks, quality control in food processing, medical diagnosis and testing, fabrication and manufacture of commercial and industrial goods, pharmaceutical production, testing or evaluating any odorant or analyte in any medium (e.g., fuel, oil, wine, solvents), and many other applications. An instrument for analyte detection would be highly desirable in many industries and applications, such as the chemical, petrochemical, food, fragrance, medical, automotive, military, environmental, health and safety, and air quality monitoring sectors. Therefore, it is desirable to develop techniques and devices for the detection of analytes.

One approach for sensing analytes is the use of an array of sensors on a substrate. Each sensor has a chemical compound which has a particular electrical characteristic response to exposure to an analyte, such as an odor. The sensors are connected to electrical circuits by which the responses of the chemical compounds to the analyte are retrieved. See, for example, U.S. application. Ser. No. 09/130,775, entitled "SENSOR ARRAYS ON AN IC FOR ANALYTE DETECTION," filed Aug. 7, 1998 and assigned to the present assignee, and which is incorporated by reference herein. Each site responds to a broad class of stimuli, with the collective response of the many different members of the sensor array providing a fingerprint of an analyte of interest. The number of data points generated for each analyte is large. Even with modern high-speed computers, the amount of data generated may significantly slow operations to analyze the sensed analytes under real world constraints, in particular. Therefore, there is a need for techniques and systems which are computationally efficient in determining or resolving an analyte upon detection from the large amount of data derived from the sensor array.

The present invention is directed toward such a technique and system for quickly and efficiently resolving analytes. A quantitative metric is generated for the effective resolution of different analytes by the sensor array. The present invention further provides a powerful tool in the analysis and construction of olfactory sensor arrays.

SUMMARY OF THE INVENTION

The present invention provides for a method for distinguishing different odors by the steps of disposing a plurality of d sensors in an array, each sensor having different electrical responses to different orders; exposing the sensors to first and second odors; generating first and second sets of data points from each of the sensors, each set corresponding to the first or second odor, each data point being represented by a vector in a d-dimensional space; determining an axis in the d-dimensional space, the axis having the property that projections of the data points onto the axis in the d-dimensional space have optimal separation; and resolving the first odor from the second odor by the separation.

BRIEF DESCRIPTION OF THE DRAWINGS

FIG. 4A is a table of pairwise resolution factors obtained from an array of fourteen carbon black polymer-composite detectors for nineteen solvent analytes; FIG. 4B is a table of pairwise resolution factors obtained from an array of eight tin oxide detectors for the nineteen solvent analytes; FIG. 4C is a table of pairwise resolution factors obtained from an array of twelve bulk conducting organic polymer detectors for the nineteen solvent analytes;

FIG. 5 is a table of normalized pairwise resolution factors obtained from the array of fourteen carbon black-polymer composite detectors;

FIG. 6 is a table of principal components of the fourteen element carbon black-polymer composite detector response data;

FIG. 10 is a table of the results of resolving on average and resolving the worst-resolved analyte pair using combined arrays of carbon black-polymer composite, tin oxide, and conducting organic polymer sensors.

DESCRIPTION OF THE SPECIFIC EMBODIMENTS

Figure 1:
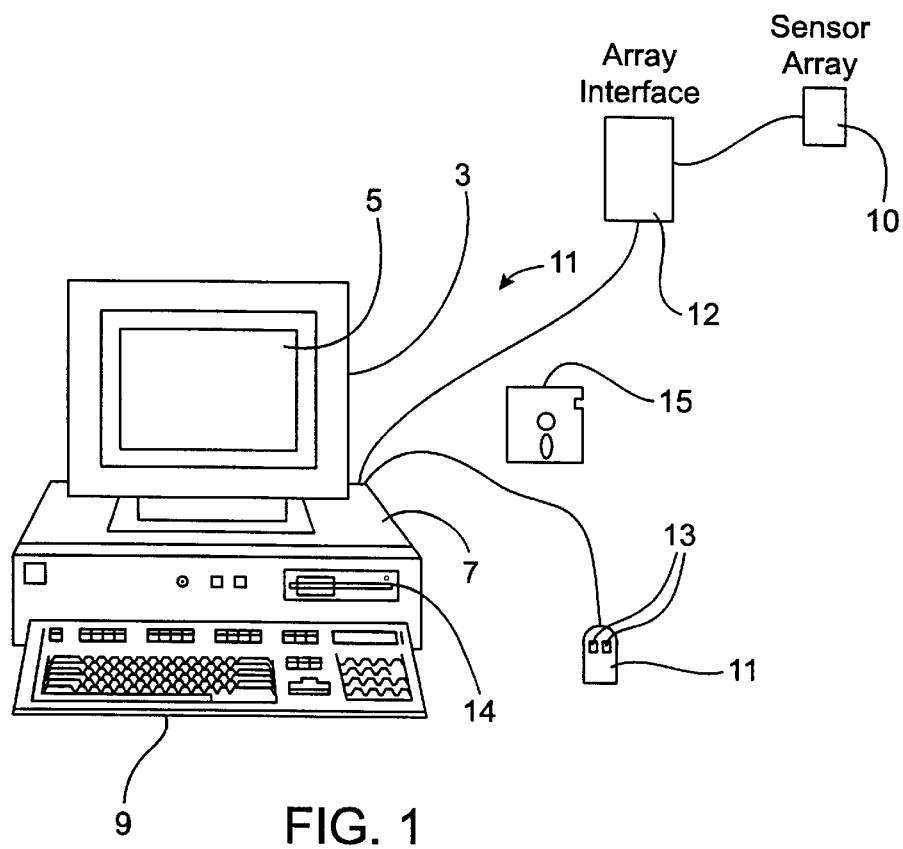
FIG. 1 illustrates an array of sensors connected to a computer unit, in accordance with one aspect of the present invention.

In accordance with the present invention, an array 10 of sensors is disposed on a substrate, such as shown in FIG. 1. Each sensor is responsive to different odor analytes in a particular manner so that the response of all the sensors creates a "fingerprint" which can be used to identify the analyte. These sensors may include surface acoustic wave (SAW) devices, tin oxide detectors, conducting organic polymers, dye-impregnated polymer films on fiber optic detectors, polymer-coated micromirrors, quartz crystal microbalances (QCMs), electrochemical gas detectors, chemically sensitive field-effect transistors, carbon black-polymer composite chemiresistors, micro-electro-mechanical system (MEMs) devices, and micro-opto-electro-mechanical system (MOEMs) devices. If the devices are compatible, the sensors might be placed on a single substrate, such as that of semiconductor material, for the benefits of miniaturization and convenience. Each of the sensors is connected by wires through an array interface 12 to a computer unit 1 which receives the electrical responses from the sensors upon exposure to an odor analyte. The computer unit is programmed to save and process the data in accordance with the data processing steps set forth below. The results may be displayed on a screen 5 of the computer unit's monitor and/or saved in memory, such as represented by a computer disk 15.

With d sensors 11 in the array 10, each sampling of the array creates d values, i.e., each sampling data point can be considered a d-dimensional vector. If there are eight sensors, each data point has eight values, one from each sensor. Hence it can be readily uhderstood that the amount of data generated by the array 10 can be quite large. For example, if there are 100 sensors in the array 10, then each data point has 100 associated values. Furthermore, there may be several samples taken for each analyte thereby magnifying the computational problem of analysis. The present invention reduces the problem of d-dimensional data point vectors to the comparison of values in one dimension. This is performed by the application of the Fisher linear discriminant to the data. In this manner the resolution of different odor analytes can be made efficiently and effectively with a quantitative metric.

In the description below, specific types of sensors or detectors (tin oxide, conducting organic polymer and carbon black-polymer composite detectors) are described with respect to the detection of specific analytes (some nineteen different solvent vapors including 1,2-dimethoxyethane, acetone, acetonitrile, anisole, benzene, butylamine, chloroform, cyclohexane, dichloromethane, ethanol, ethyl acetate, isopropanol, methanol, n-heptane, n-pentane, tetrahydrofuran, toluene, triethylamine and $\alpha,\alpha,\alpha$-trifluorotoluene). It should be understood that the present invention described herein is applicable to other sensors, including those of different sensing modalities, and analytes.

The present invention might best be understood by assuming a typical experiment where it is desired to obtain a quantitative measure of the efficiency of an array of 14 detectors in distinguishing between two solvents. The array is exposed to each solvent for 12 cycles. Each cycle consists of 300 seconds of pure carrier gas over the detector array, then 240 seconds of gas and the solvent, then 300 seconds of pure carrier gas again. This procedure ensures steady state conditions before, during, and after, exposure to the solvent mixture. The resistance of each detector, j, is measured at 3 second intervals throughout each exposure, i. The experiment data base for this typical experiment thus consists of 2*12*840/3*14=94,080 resistance measurements.

Figure 2:
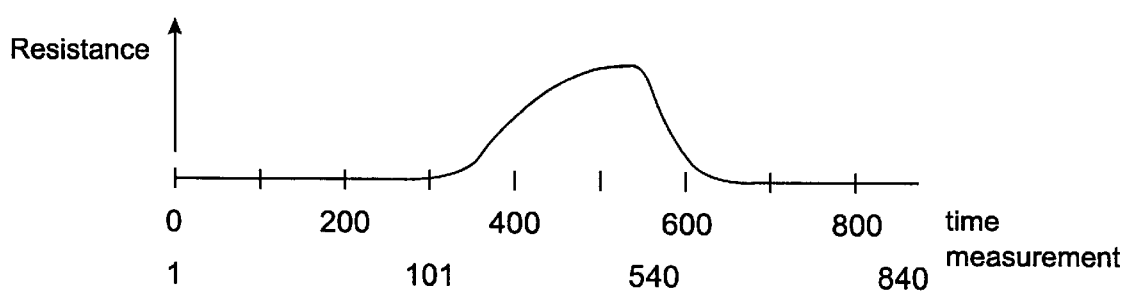
FIG. 2 illustrates a typical electrical response of a sensor to the presence of an analyte.

The first step in processing these data finds the maximum relative resistance change during each exposure for each solvent and each detector. Of course, it should be understood that the present invention is also applicable to other electrical parameters, such as voltage, current, capacitance, or inductance, which might vary in response to the exposure to analytes. A typical detector response during an exposure will have the general form, such as illustrated in FIG. 2. The baseline resistance, $R_b$, is the stable value attained by the detector just prior to the introduction of the solvent into the carrier gas stream, that is, the $100^{th}$ measurement (300 seconds sampled at 3 second intervals). The maximum resistance value attained during the gas and solvent interval, $R_{max}$, is readily obtained between measurements 101 and 540 (typically towards the end of the 240 second gas and solvent interval). The maximum relative resistance change for the cycle is then:

$$(R_{max}-R_b)/R_b.$$

The experimental database has now been reduced to 2*12*14=336 measurements. These can be regarded as a set of twelve 14-dimensional points, $\alpha_{ij}$ (i=1 to 12 and j=1 to 14), for each solvent. That is:

$$\alpha_{ij} = \begin{pmatrix} \alpha_{11} \\ \alpha_{12} \\ \vdots \\ \alpha_{1,14} \end{pmatrix}, \begin{pmatrix} \alpha_{21} \\ \alpha_{22} \\ \vdots \\ \alpha_{2,14} \end{pmatrix}, \dots, \begin{pmatrix} \alpha_{12,1} \\ \alpha_{12,2} \\ \vdots \\ \alpha_{12,14} \end{pmatrix}$$

A quantitative measure of the array efficiency in distinguishing between the solvents is obtained using the optimum resolution factor (defined by Fisher's linear discriminant):

$$rf = \frac{d_{\bar{w}}}{\sqrt{\sigma_{a,\bar{w}}^2 + \sigma_{b,\bar{w}}^2}}$$

The resolution factor, rf, is from an optimal projection vector, w, where $$w = S_w^{-1}(m_a - m_b)$$

where $m_a$ and $m_b$ are the respective 14-dimensional means of each of data sets of the two solvents, that is:

$$m = \begin{pmatrix} m_1 \\ m_2 \\ \vdots \\ m_{14} \end{pmatrix} = \frac{1}{12} \begin{pmatrix} \sum \alpha_{i1} \\ \sum \alpha_{i2} \\ \vdots \\ \sum \alpha_{i,14} \end{pmatrix} = \frac{1}{12} \begin{pmatrix} \alpha_{1,1} + \alpha_{2,1} + \ldots + \alpha_{12,1} \\ \alpha_{1,2} + \alpha_{2,2} + \ldots + \alpha_{12,2} \\ \vdots \\ \alpha_{1,14} + \alpha_{2,14} + \ldots + \alpha_{12,14} \end{pmatrix}$$

The within-class scatter matrix, $S_w$, is the sum of the matrices $S_a$ and $S_b$ where $$S = \Sigma (x_{ij} - m)(x_{ij} - m)^T$$

Each S is the sum over the 12 exposures of 14*14-dimensional terms, such as:

$$\begin{pmatrix} \alpha_{11} - m_1 \\ \alpha_{12} - m_2 \\ \vdots \\ \alpha_{1,14} - m_{14} \end{pmatrix} (\alpha_{11} - m_1 \quad \alpha_{12} - m_2 \quad \ldots \quad \alpha_{1,14} - m_{14})$$

Then $$S_w = S_a + S_b; \text{ and}$$

$$w = S_w^{-1}(m_a - m_b)$$

$d_w$ is the distance along the vector w between the projected means and is computed as:

$$d_w = [w^*(m_a - m_b)(m_{a-mb})^T]^{1/2}$$

Also, the denominator for rf is:

$$w^T S w = \sqrt{\sigma_{a,w}^2 + \sigma_{b,w}^2}$$

to obtain the resolution factor, rf, between two solvents.

Figure 3:
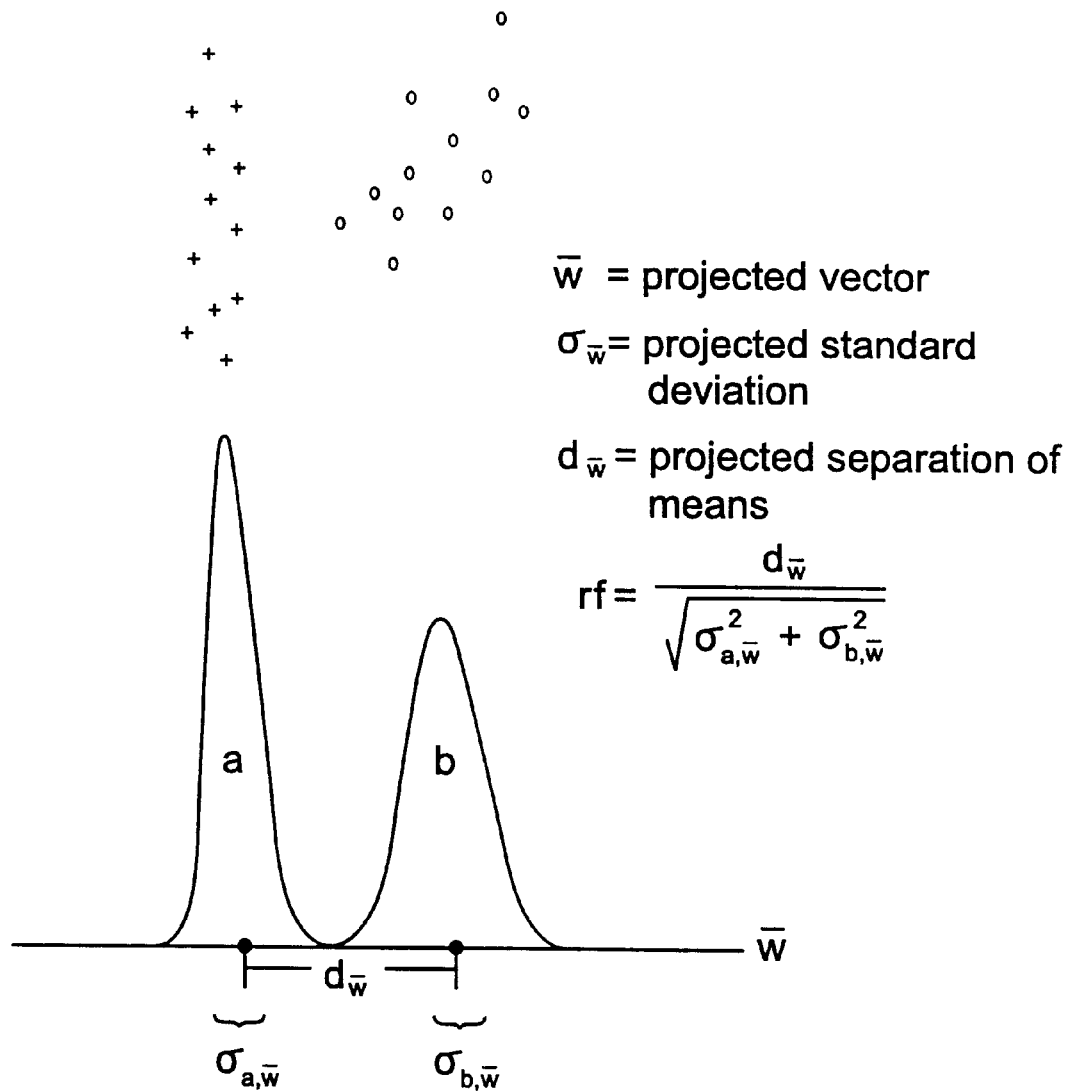
FIG. 3 is a two-dimensional representation of the resolution factor obtained by the projection of the data points of two analytes upon optimal projection vector, according to one aspect of the present invention.

Stated differently, the Fisher linear discriminant searches for the projection vector, w, in the detector space which maximizes the pairwise resolution factor, i.e., rf, for each set of analytes, and reports the value of rf along this optimal linear discriminant vector. FIG. 3 is a graphical two-dimensional representation of the data points of analytes a and b, and their projected means along the optimal discriminant vector w. The rf value is an inherent property of the data set and does not depend on whether principal component space or original detector space is used to analyze the response data. This resolution factor is basically a multi-dimensional analogue to the separation factors used to quantify the resolving power of a column in gas chromatography, and thus the rf value serves as a quantitative indication of how distinct two patterns are from each other, considering both the signals and the distribution of responses upon exposure to the analytes that comprise the solvent pair of concern. For example, assuming a Gaussian distribution relative to the mean value of the data points that are obtained from the responses of the array to any given analyte, the probabilities of correctly identifying an analyte as a or b from a single presentation when a and b are separated with resolution factors of 1.0, 2.0 or 3.0 are approximately 76%, 92% and 98% respectively.

The efficacy of the technique is demonstrated in the empirical data obtained with arrays having different types of detectors, i.e., tin oxide, conducting organic polymer and carbon black-polymer composite detectors. In the experiments, the array of tin oxide detectors had eight different detectors; the array of conducting organic polymer detectors had twelve different detectors; and the array of carbon block-polymer composite detectors had fourteen different detectors. Nineteen different solvent vapors (1,2-dimethoxyethane, acetone, acetonitrile, anisole, benzene, butylamine, chloroform, cyclohexane, dichloromethane, ethanol, ethyl acetate, isopropanol, methanol, n-heptane, n-pentane, tetrahydrofuran, toluene, triethylamine and α,α, α-trifluorotoluene) were used as the analytes.

FIGS. 4A–4C display the pairwise resolution factors, rf, for the three different types of detector arrays. The table in FIG. 4A presents the resolution factors obtained from an array of the fourteen carbon black-polymer composite detectors for all 171 pairs of the nineteen vapors. The tables in FIGS. 4B and 4C display similar data for the eight tin oxide detectors and for the twelve available bulk conducting organic polymer detectors which had all been exposed to the nineteen test solvent vapors.

These resolution factors allow assessment of the performance of the different arrays, or of the performance of subsets of the arrays, in various sensing tasks. Two criteria are chosen as measures of array performance: (1) the average ability to resolve all analyte pairs, $\overline{rf}$, and (2) the ability of the array to resolve the worst-resolved analyte pair, $rf_{worst}$. The $\overline{rf}$'s and standard deviations across all analyte pairs for the full carbon black-polymer composite, tin oxide, and conducting polymer arrays (FIGS. 4A–4C) evaluated were 145±93, 27±23 and 18±16 respectively, while the $rf_{worst}$ values were 23, 4.0 and 1.4, respectively. Based on this analysis, the carbon black-polymer composite array yielded the largest mean statistical separation of the response patterns produced by exposure of this particular collection of available detectors to this particular collection of test solvent vapors exposed at fixed concentrations. Using the same experimental conditions, the carbon black composite detector array also yielded the largest separation between the worst-resolved pair of analytes.

The present invention also provides a means of determining the resolving power of the carbon black-polymer composite detectors at variable analyte concentrations. The analysis described above serves as one quantitative measure of the classification ability of different detector arrays. However, this metric also includes any separation between data clusters that arises from the differences in the amplitudes of the array response to the vapors in the test analyte set. Two solvents that produce nearly identical patterns, but with very different absolute detector response amplitudes, would produce two well-separated clusters. The large pairwise Devalue for such a solvent pair produced by the data analysis method described above is relevant for tasks in which the concentration of an analyte is known, or when only detection of changes over time in an otherwise relatively constant analyte composition is of interest. However, such a data analysis procedure is clearly not appropriate for assessing array classification performance in applications where the concentration of the analyte is not known, or not known to be fixed, in advance.

A measure of array performance under such conditions requires that the fundamental differences in patterns produced by the various vapors be determined without considering differences in the mean magnitude of the detector responses. Carbon black-polymer composite detectors containing ≧20% by weight carbon black have been shown to respond linearly to the concentration of several test analytes over at least an order of magnitude of analyte concentration. Hence, a measure of the concentration-independent ability of the array to classify the various solvents in the test can be obtained for the carbon black-polymer composite detectors by normalizing the array responses. This procedure is equivalent to adding an extra degree of freedom, analyte concentration, to the classification task.

The normalized response, $N_{ij}$, of the $j^{th}$ detector in an n detector array to the $i^{th}$ of k exposures of a specific analyte is defined as:

$$N_{ij} = \frac{\Delta R_{ij,\max}/R_b}{\frac{1}{n \cdot k}\sum_{j,i}(\Delta R_{ij,\max}/R_b)},$$

where the summation is over the response of all n detectors to all k exposures of the specific analyte. For the carbon black-polymer composite vapor detectors, a comparison of the 171 pairwise resolution factors obtained from normalized responses (the table in FIG. 5) to those obtained only from raw response data (the table in FIG. 4A) shows that allowing the vapor concentration to be a floating variable slightly reduces, but does not remove, the array's ability to resolve the various test analytes at the concentrations used in this study. Thus, the $\overline{rf}$ decreased from 145±93 to 102±50 when the data were normalized. This analysis can be used for other detectors which exhibit responses that are linear with changes in analyte concentration.

The empirical data also allows comparison of the resolving power of different detector arrays with the same number of detectors at known analyte concentrations. This allows comparison between the performance of different types of arrays without possible biases due to differing numbers of detectors in each type of system. Thus, the data obtained from the specific carbon black-polymer composite detector array having the median $\overline{rf}$ of all possible combinations of twelve of the fourteen carbon black-polymer composite detectors studied are compared to the data produced by the available twelve element conducting polymer detector array. Similarly, arrays of carbon black-polymer composite, bulk organic conducting polymer, and tin oxide detectors are compared at a common array size of eight detector elements. In these comparisons, unnormalized data are used because the lack of linearity with varying analyte concentration of some of the detector modalities prevent meaningful normalization of the detector response data in those instances.

The carbon black-polymer composite detector array having the median $\overline{rf}$ of all possible combinations of twelve of the fourteen carbon black-polymer composite detectors consist of polymers #2 and 4–14 (refer to the table in FIG. 6). This particular array displayed $\overline{rf}$=117±79 for the unnormalized response patterns to the set of test analytes at the fixed concentrations. For comparison, the available twelve element bulk organic conducting polymer array produce $\overline{rf}$=27±23 for this same task.

The three detector arrays are also compared in resolving power using eight element arrays. The $\overline{rf}$ value using unnormalized data for the eight tin oxide detectors was 27±23, while that for the median-performing eight element carbon black-polymer composite array (detectors #3, 6–10, 12 and 13 from the table in FIG. 6) is 62±32 and that of the median-performing eight element bulk conducting organic polymer array (detectors #1–4, 6, 7, 10 and 11 as labeled by the manufacturer Neotronics, Inc.) is 13±10. The trends in $\overline{rf}$ values observed for twelve element arrays is thus also present at smaller array sizes, for the set of tasks and sets of detectors evaluated.

Rather than the average resolving power $\overline{rf}$, the resolution between the two poorest-resolved solvent pairs may be used to measure the performance of the arrays. To obtain this type of comparison, the array having the median $rf_{worst}$ of all possible combinations of twelve of the fourteen carbon black-polymer composite detectors was compared to the $rf_{worst}$ value of the available twelve detector conducting polymer array. The selected twelve element carbon black-polymer array contained detectors #1–3, 5 and 7–14 and displayed $rf_{worst}$=20 (for anisole vs. butylamine), whereas the twelve element conducting polymer array yielded $rf_{worst}$=1.4 (for n-heptane vs. α,α,α-trifluorotoluene). Using a set of only eight detectors allowed a comparison between all three types of detector modalities. Using this metric, the median-performing eight element carbon black-polymer composite array (detectors #2, 4, 5 and 8–12) had an $rf_{worst}$=11 (anisole vs. butylamine) and the eight element tin oxide array had an $rf_{worst}$ of 3.8 (for butylamine vs. triethylamine), while the median-performing eight element bulk conducting organic polymer array (detectors #1, 2, 4–6, 9, 10 and 12) had an $rf_{worst}$=1.0 (n-heptane vs. α,α,α-trifluorotoluene).

The data can also used to determine whether the combination of different sensor types realize significant improvement in the resolving power of the test solvents. The results of the combined arrays in resolving the nineteen analytes on average, and in resolving the worst-resolved pair, are shown in the table of FIG. 10. All pairwise combinations of complete (fourteen element carbon black-polymer composite, twelve element conducting organic polymer, and eight element tin oxide) arrays of different sensor type, are investigated, along with the performance of the full combination of all three arrays of different sensor types. To analyze the data in a consistent fashion for different arrays and vapors, autoscaled response data are used to formulate the resolution factors. The autoscaled response of the jth sensor to the ith exposure, $A_{ij}$, is:

$$A_{ij} = \frac{(\Delta R_{ij,\max}/R_b) - \mu_j}{\eta_j}$$

where $\mu_j$ and $\eta_j$ represent the mean and standard deviation, respectively, of the maximum relative differential resistance response of the jth sensor to the entire group of analytes.

A slight improvement in $\overline{rf}$ from 9.7 to 9.8 is observed when the twelve available conducting organic polymer sensors are added to the fourteen element carbon black-polymer composite sensor array. The $rf_{worst}$ increases more significantly, from 0.91 to 1.8, when these sensors are added. All other combinations of the full arrays, including the addition of the eight tin oxide sensors to the twenty-six sensor carbon black-polymer composite and conducing organic polymer sensors, underperform the twenty-six sensor array's performance for this set of test solvents using autoscaled sensor response data. An explanation of the observed performance improvement by adding the bulk organic conducting polymer sensors to the carbon black-polymer composite sensors is that the latter set is weakest at resolving some polar analytes, while the more polar bulk organic conducting polymer sensors are strong in resolving polar analytes. The combination of the two sensor types, in this case, improves the balance in chemical properties of the polymers in the sensor array and thus slightly improves the ability of the array to resolve this particular set of analytes.

The data can also be used to evaluate array performance as a function of the number of detectors in the array to determine how many detectors are required for various tasks. Both $\overline{rf}$ and $rf_{worst}$ are evaluated for all possible combinations of one through fourteen detectors in the carbon black-polymer composite detector array, one through eight detectors in the tin oxide array, and one through twelve detectors in the bulk organic conducting polymer array. One goal would be to construct the array that has the best average resolution between any pair of vapors that it might encounter. This criterion is closely related to the goal of constructing the array with the most chemical diversity, so that it best separates any set of vapors that is likely to be in the environment. To assess the diversity of the detector elements in a given detector modality, for all possible combinations of every n-element array of each detector type, the average pairwise resolution factor, $\overline{rf}(n)$, is computed for all 171 different solvent pairs of the nineteen solvents. The value of $\overline{rf}(n)$ for each allowed combination is tabulated, and the average value of $\overline{rf}(n)$ for all possible combinations having the specified number of detectors is plotted vs. the number of detectors in the array. The computed quantity is thus a statistically-based measure of the average pairwise resolution of the solvents in the nineteen vapor test set that would be obtained from the average, unbiased and unsorted data arising from an n-element detector array of a given detector modality.

Figure 7A:
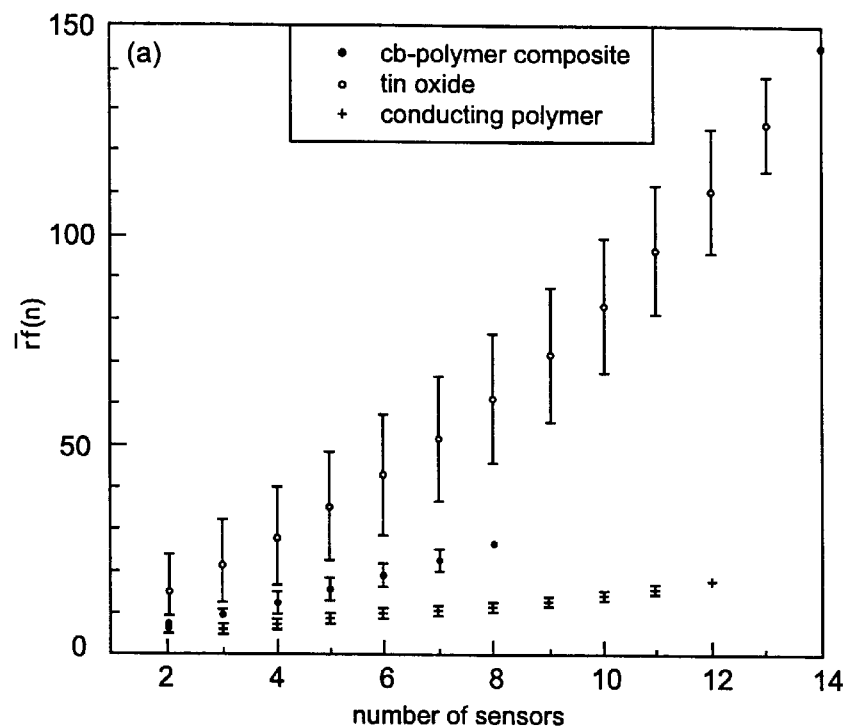
FIG. 7A is a plot of the average ability to resolve all analyte pairs, $\overline{rf}(n)$, versus the number n of sensors in the array.
Figure 7B:
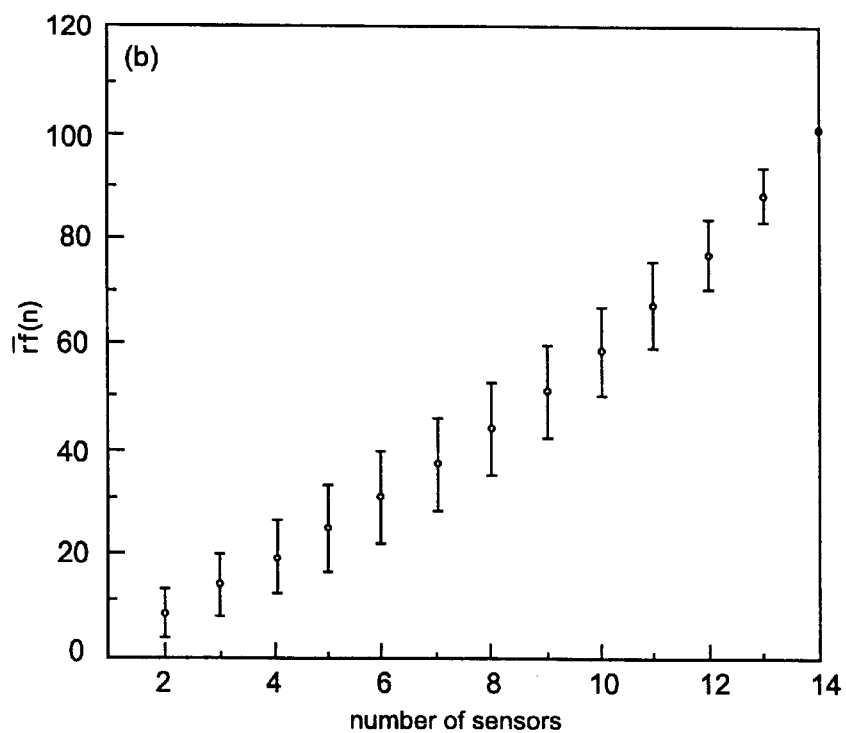
FIG. 7B is a plot of the average ability to resolve all analyte pairs, $\overline{rf}(n)$, for the carbon black-polymer composite detectors versus the number n of sensors in the array using normalized data.

As displayed in FIG. 7A, these data show that, for all three detector arrays, the average resolving power of the array increased as the numbers of detectors in the array increased. Thus, for situations in which the sensing task is not known in advance, such as in quality control applications or in complex environments with varying backgrounds, the average performance of these tested detector arrays improved as the number of different detectors increased. For both raw response data and normalized data for the carbon black-polymer composite detectors, whose signal linearity vs. analyte concentration behavior permitted such an analysis to be performed in this test system, the same trend was observed for this particular array with this particular set of test analytes (as shown in FIG. 7B).

Figure 7C:
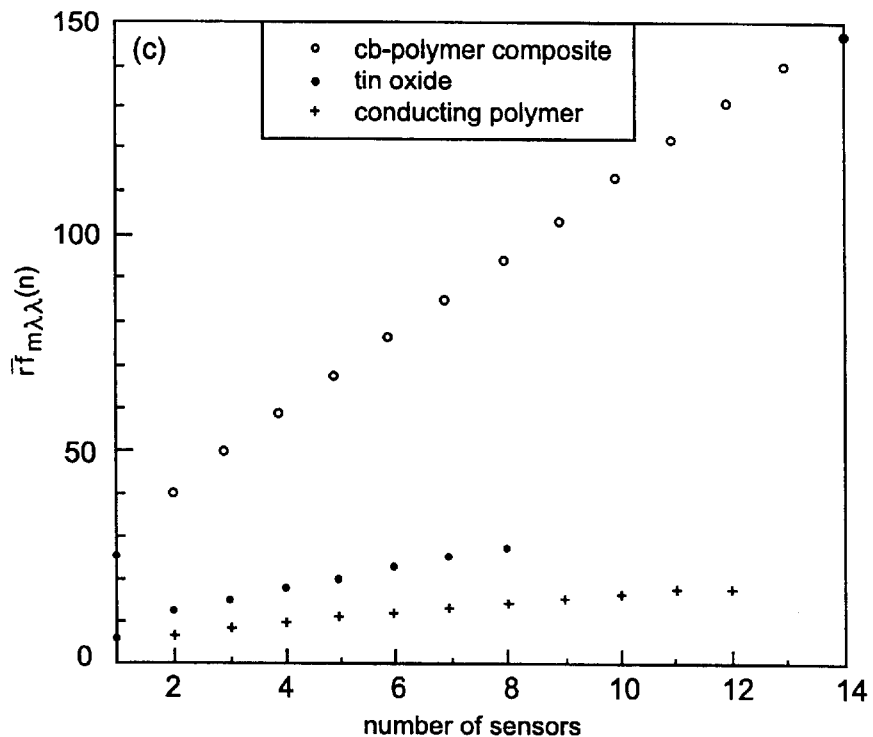
FIG. 7C is a plot of the maximum average resolution factor, $\overline{rf}max(n)$, the specific set of specified number n of detectors which have the largest ability on average to resolve all solvent vapor analyte pairs versus the number of detectors n.

At any array size and for any of the detector arrays investigated, subsets of the full array that can outperform the mean $\overline{rf}(n)$ performance of all possible combinations of elements having that specific array size can always be identified. Analysis provides an answer to the question, given that the task to best resolve on average all nineteen specific test vapors, whether the best performing array contains the full collection of available detectors or instead only contains subsets of each detector modality. The quantity that is evaluated is the average pairwise resolution factor, determined using the Fisher linear discriminant method, of the best-performing set of detectors in an array, $\overline{rf}_{max}(n)$, at each number of detectors, n. FIG. 7C depicts the $\overline{rf}_{max}(n)$ data for each of the three detector modalities using raw response data. For each of the three detector modalities, a larger number of detectors provides increased resolving power according to the $\overline{rf}_{max}(n)$ criterion.

Figure 7D:
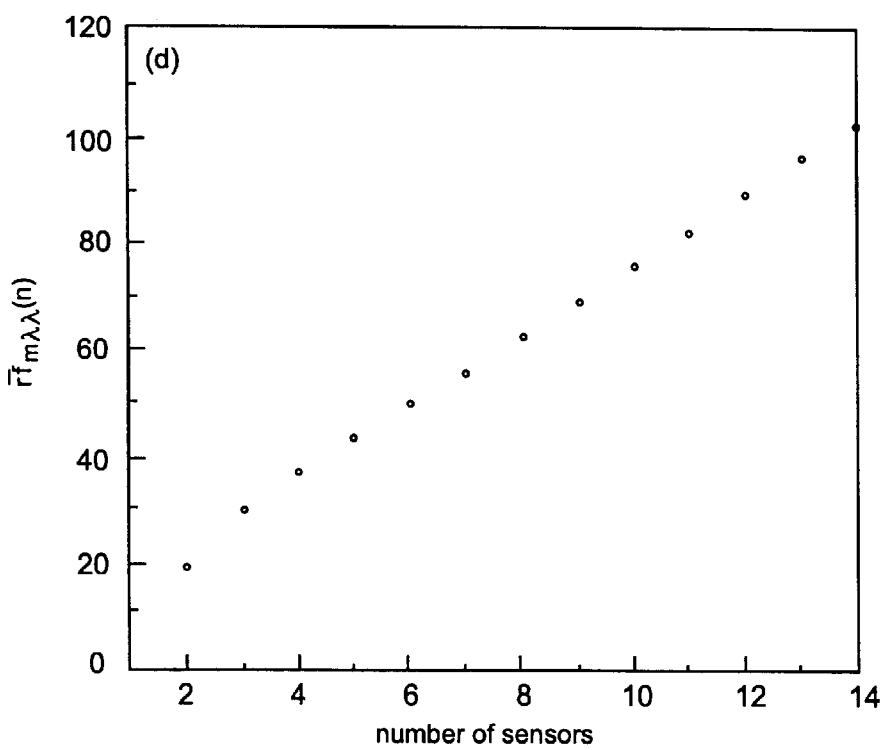
FIG. 7D is a plot of the maximum average resolution factor, $\overline{rf}max(n)$, for the carbon black-polymer composite detectors versus the number of detectors n using normalized data.

In the case of the carbon black-polymer composite detectors, it is also possible to evaluate the concentration-independent performance using normalized data. As displayed in FIG. 7D, the optimum set of detectors obtained under these criteria once again is the full fourteen-detector array.

Figure 8A:
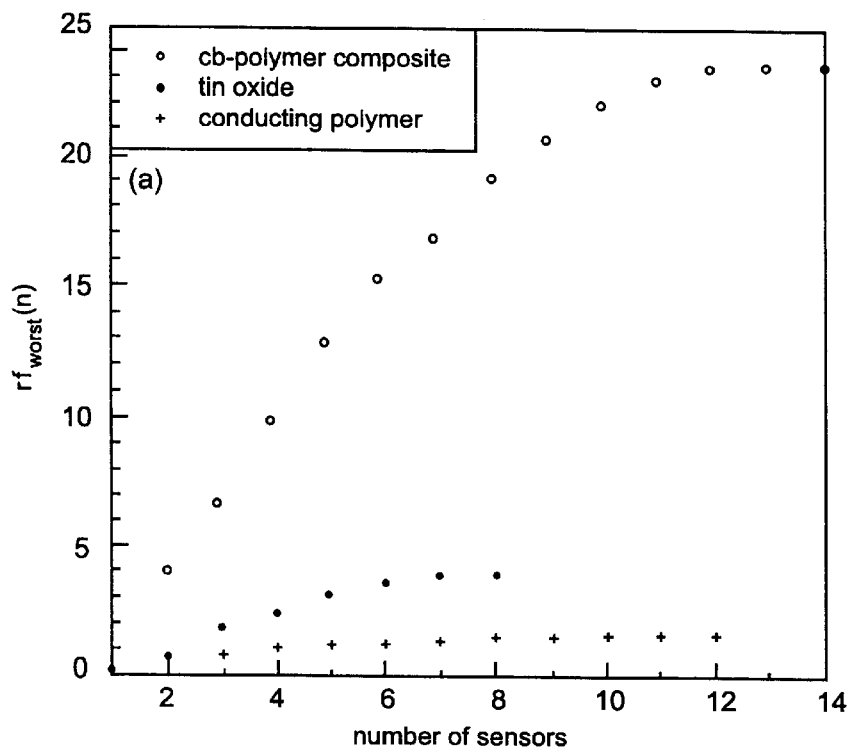
FIG. 8A is a plot of the smallest pairwise resolution factor, $rf_{worst}$, versus the number n of sensors in the array.

Another goal might be the selection of the subset of detectors that maximized the smallest pairwise solvent resolution factor for the analytes in the test set. The data in FIG. 8A describe the ability of each array type to resolve the worst-resolved analyte pair as a function of the size of the detector array. For each of the three detector types, the resolving power increases rapidly and then appears to plateau at large numbers of detectors. However, in none of the three cases, using raw response data to analytes at fixed concentrations, does the addition of an extra detector diminish the resolving power of the array.

The array of eight tin oxide detectors maximizes the $rf_{worst}$ at 3.8 (for butylamine vs. triethylamine). This $rf_{worst}$ corresponds to approximately a 99% confidence in correctly distinguishing between the two analytes in a single presentation to the array. The array of twelve bulk conducting organic polymer detectors maximizes the $rf_{worst}$ at 1.4 (for n-heptane vs. α,α,α-trifluorotoluene). This corresponds to approximately an 84% confidence in correctly distinguishing between the two analytes on a single presentation to the array. The array of fourteen carbon black-polymer detectors maximizes $rf_{worst}$ at 23. For this best set of fourteen detectors, the worst resolved analyte pair is anisole and butyl amine. The $rf_{worst}$ of 23 essentially corresponds to a 100% confidence in distinguishing between the two analytes in a single presentation to the detector array.

Figure 8B:
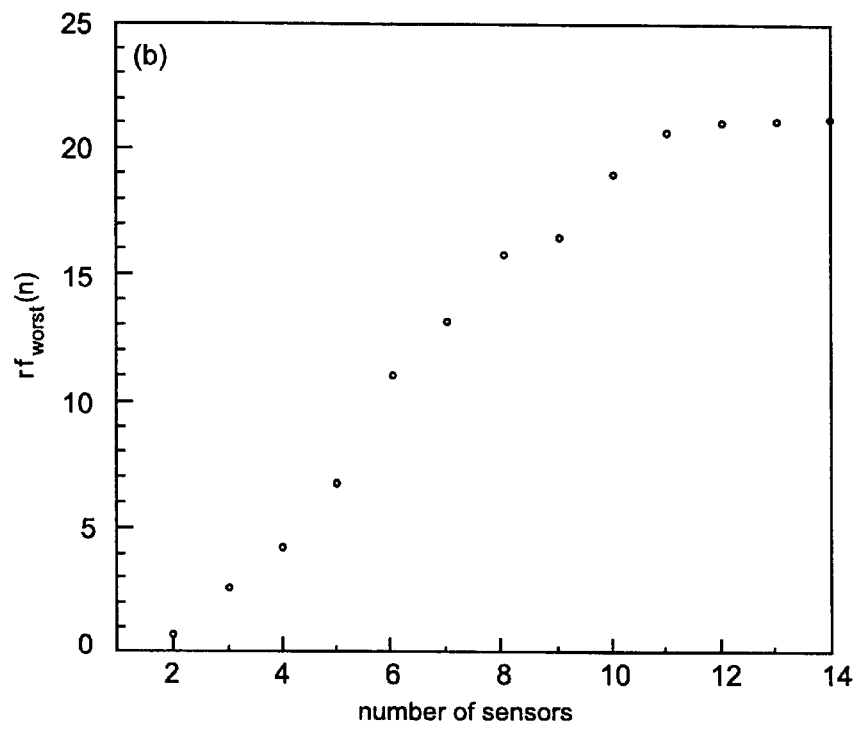
FIG. 8B is a plot of the smallest pairwise resolution factor, $rf_{worst}$, versus the number n of carbon black-polymer composite sensors in the array.

FIG. 8B depicts $rf_{worst}$ values for normalized data for the carbon black-polymer composite detectors. Again, the best resolution is maximized by the full fourteen detector array, although the data appears to plateau for sets containing more than eleven detectors. The full fourteen-detector set maximizes $rf_{worst}$ at 21 (for butylamine vs. n-pentane), which essentially corresponds to a 100% resolution probability. This full set of fourteen carbon black-polymer composite detectors contains polymers which vary widely in chemical properties, from the polar poly(N-vinylpyrrolidone) to the comparatively non-polar poly(ethylene-co-vinyl acetate), and includes halogenated and aromatic functional groups such as those in poly(vinylidene chloride-co-acrylonitrile) and poly(9-vinylcarbazole). The diversity in the detector component properties, which matches well with the diversity in the analytes, leads to the ability to resolve all the nineteen analytes in the test set quite effectively.

The present invention also allows analysis in the situation where the task is known and can be specified precisely in advance of array construction. Members of the detector array can, in principle, be pre-selected to provide the optimum performance for the task of concern. The issue to be addressed is whether the optimal resolution of a specific solvent pair, at a fixed concentration, is obtained through use of the data produced by the full array, or whether it is advantageous, for that particular pair of analytes, to use only the data produced by a subset of the full detector array. Ideally, all detectors would be orthogonal and one detector would probe exactly along the direction that is associated with maximizing the chemical differences between the two specific analytes. This single detector, and duplicates of it, should form the best "array" for resolving the two test analytes, under controlled conditions, at fixed concentrations.

However, since in reality the vapor detectors are not generally mutually orthogonal, nor do they probe exactly the chemical differences between a specific analyte pair, it is probable that a few specific, partially correlated, detectors will combine to resolve a specific analyte pair better than any single detector in the array.

Figure 9:
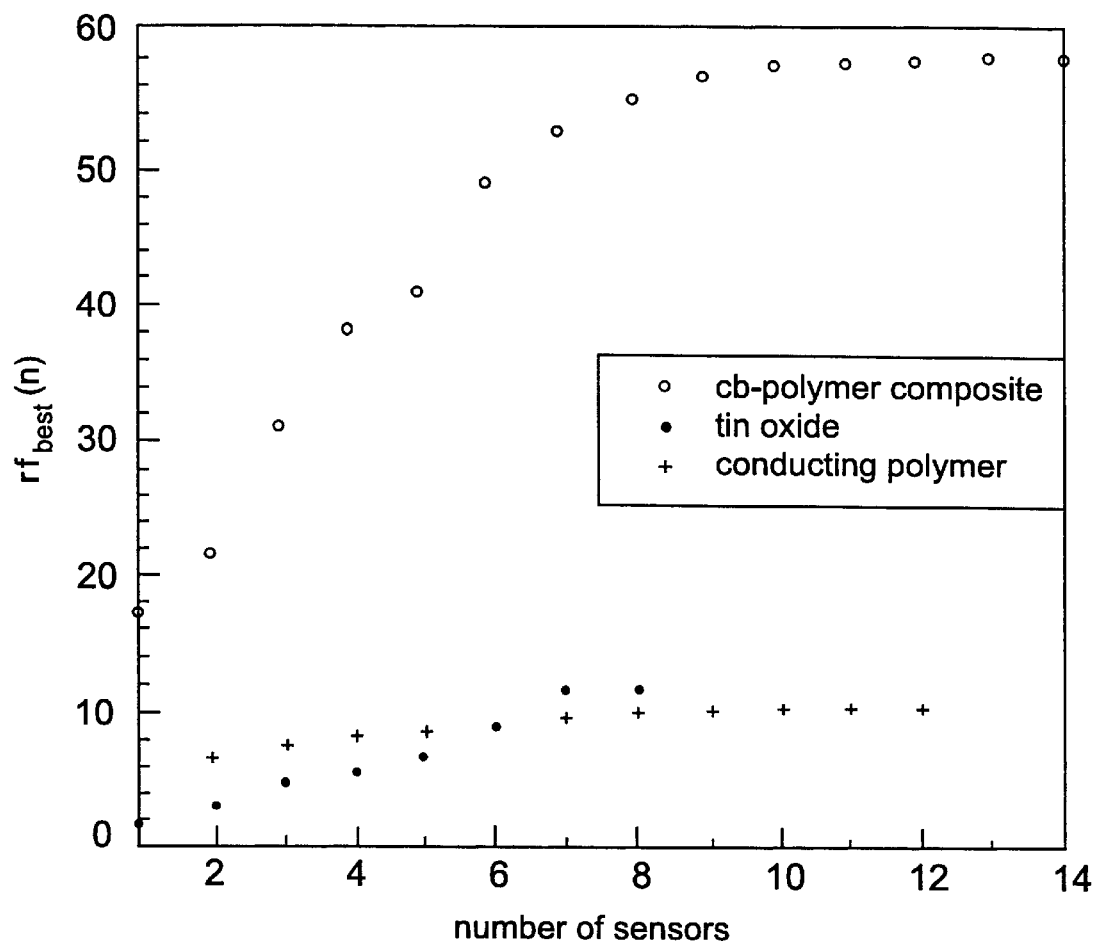
FIG. 9 is a plot of the largest solution factor, $rf_{best}(n)$, to resolve ethyl acetate from tetrahydrofuran at fixed concentrations for all combinations of detectors from the number n of the detectors in the array versus the number n of the detectors in the array.

As a representative example, FIG. 9 depicts the results for resolving an arbitrarily chosen solvent pair, ethyl acetate from tetrahydrofuran, as a function of the size of the detector array, using only raw response data. All possible combinations of n detectors in the array are investigated for the fourteen detector carbon black-polymer composite array, the eight detector tin oxide array, and the twelve detector bulk conducting organic polymer array. Only elements from a given detector array are allowed to form the desired detector array (i.e., carbon black composites, tin oxide detectors, and bulk conducting organic polymers are restricted to be in mutually separate arrays for this analysis). For each specific number of detectors in the array, only the best resolution factors that resulted from the optimal array for the task of separating ethyl acetate from tetrahydrofuran, $rf_{best}(n)$, are plotted.

In each of the three cases, the ability of the arrays to resolve ethyl acetate from tetrahydrofuran increases as additional detectors are included. From FIG. 9, it is apparent that beyond approximately the first six carbon black-polymer detectors (#8–13 from the table in FIG. 6), additional detectors provide minimal increases in the resolution of ethyl acetate from tetrahydrofuran. Five of these six carbon black-polymer composite detectors contain polymers with one or both of the ether and ketone functionalities present in the ethyl acetate and tetrahydrofuran analytes, which explains chemically why the detectors perform well in this specific task. The other detectors in the array produce response data along vectors that do not lie as close to the vector that best separated these two solvents in detector space.

A similar metric is evaluated for all other solvent pairs as well. For each array class, using raw response data, the full array maximizes the resolution of each analyte pair. The best resolution factor that is obtained between any vapor pair, using any set of detectors of the same class, is obtained for distinguishing n-pentane from toluene using the carbon black-polymer composite detector array which has rf=556 using unnormalized data for this task. Similarly, using normalized data from the carbon black-polymer composite detector array, the best resolved analyte pair is dichloromethane from α,α,α-trifluorotoluene with rf=256. The largest resolution factors obtained between any analyte pair, using raw response data, for the conducting polymer or tin oxide detectors are 77 (for ethanol vs. isopropanol) and 148 (for chloroform vs. toluene), respectively, again for unnormalized data.

One of the findings to which the present invention leads is that array performance increases, in general, as the number of sensors increases. The larger number of sensors is beneficial for resolving, on average, a generalized set of test vapors which might not all be known in advance of the array design. A larger number of sensors should increase the probability that the dimensionality of odor space is fully spanned by the array. Stated differently, the array should be able to probe many chemical differences between analytes. On the other hand, with the analytes are fixed, a smaller number of selected sensors could optically resolve between solvent pairs. An optimal number of sensors can be determined for a given set of analytes.

The present invention is also capable of quantitatively pointing to the superiority of certain types of arrays for a given set of analytes. As between the tested arrays of carbon black-polymer composite detectors, the tin oxide detectors, and conducting polymer detectors, it is clear that the carbon black-polymer composite detectors outperform the other sensor arrays. However, combining arrays of different detector of different modalities should lead to synergistic performance for the resolution of many analytes. For example, bulk organic conducting polymer detectors might be placed in an array of surface acoustic wave (SAW) devices, tin oxide detectors, dye-impregnated polymer films on fiber optic detectors, quartz crystal microbalances (QCMs), or carbon black-polymer composite chemiresistors, for example. Besides the resolution performance, choosing between these various types of sensor arrays might require consideration of more practical matter, such as the signal-to-noise ratio of a given type of a signal transduction mechanism, the ease of manufacturing the arrays and their costs, and the integration with processing electronics.

Hence the use of a numerical measurement of the resolution factor of a detector array according to the present invention can enhance the quantitative understanding of the size of the sensor array, whether adding new detectors should be added, or whether certain chemical properties are underrepresented in a specific array, for example. The present invention helps the evaluation of other factors that are important in the design of arrays of vapor detectors.

It should be noted that the Fisher linear discriminant technique described herein is one analytical approach for resolving between analytes. Another related approach is principal component analysis in which the data are transformed such that they project along mutually orthogonal vectors in n-dimensional space so that the first principal component is the vector that captures the most variance in the data set and higher principal components capture progressively less variance in the data. This statistical approach preserves the inherent weighing of the original data set in terms of molecular properties being probed by the sensors, but allows for improved visualization of the differences between the various patterns as they cluster in principal component space. In either principal component space or original, i.e., sensor, coordinate space (used in the Fisher linear discriminant technique), a statistical measure of the differences between two clusters of patterns can be obtained by determining the distance between the centroids of the data arising form repeated exposures to a given vapor and dividing this distance by the sum of the standard deviations of the two different pattern clusters projected along the vector that connects these centroid points. This metric is independent of the coordinate system chosen to display the data and is instead an inherent statistical property of the data set.

From standard vector analysis, the mean response vector, $x_a$, of an n-sensor array to analyte a is given as the n-dimensional vector containing the mean autoscaled response of each sensors, $A_{aj}$, to the ath analyte as components such that $$x_a = (A_{a1}, A_{a2}, \ldots A_{an})$$

The average separation, $|d|$, between the two analytes, a and b, in the Euclidean sensor response space is then equal to the magnitude of the difference between $x_a$ and $x_b$. The noise of the sensor responses is also important in quantifying the resolving power of the sensor array. Thus the standard deviations, $\sigma_{a,d}$ and $\sigma_{b,d}$, obtained from all the individual array responses to each of a and b along the vector d, are used to describe the average separation and ultimately to define the pairwise resolution factor as $$rf = \frac{|\overline{d}|}{\sqrt{\sigma_{a,\overline{d}}^2 + \sigma_{b,\overline{d}}^2}}$$

Further details of the present invention are described in the previously referenced U.S. Provisional Application No. 60/086,876, filed May 27, 1998 and U.S. Provisional Application No. 60/088,804, filed Jun. 9, 1998, which applications are hereby incorporated by reference for all purposes.

While the above is a complete description of the preferred embodiments of the invention, various alternatives, modifications and equivalents may be used. It should be evident that the present invention is equally applicable by making appropriate modifications to the embodiments described above. Therefore, the above description should not be taken as limiting the scope of the invention which is defined by the appended claims.

What is claimed is:

1. A method of resolving different odors, said method comprising exposing an array of odor sensors to a plurality of odors, each odor sensor having an electrical response to at least one of said odors;

determining the maximum relative electrical response for each odor and sensor, the maximum relative electrical response comprising the maximum electrical response to an odor beyond the background electrical response;

determining the average maximum relative electrical response for the maximum relative electrical responses determined for each odor;

determining the standard deviation for the average maximum relative electrical response for the maximum relative electrical responses determined for each odor; and computing the optimum resolution factor by the Fisher linear discriminant for each pair of odors.

2. The method of claim 1 wherein the optimum resolution factor-equals $$\frac{d_{\overline{w}}}{\sqrt{\sigma_{a,\overline{w}}^2 + \sigma_{b,\overline{w}}^2}}$$

where w and $\overline{w}$ are identical and w is a projection vector in a d-dimensional space, d corresponding to the number of odor sensors in the array, $\sigma_{a,w}$ is the standard deviation for the average maximum relative response for odor a along vector w, $\sigma_{b,w}$ is the standard deviation for the average maximum relative response for the odor b along vector w, and $d_w$ is the distance between the average maximum responses for odors a and b along vector w.

3. The method of claim 1 wherein said array of odor sensors includes at least four sensors.

4. The method of claim 1 wherein said array of odor sensors includes at least eight sensors.

5. The method of claim 1 further comprising disposing said sensors on a single substrate.

6. The method of claim 5 wherein said substrate comprises semiconductor material.

7. The method of claim 5 wherein said sensors comprise carbon black-polymer composite sensors.

8. The method of claim 5 wherein said sensors comprise tin oxide sensors.

9. The method of claim 5 wherein said sensors comprise bulk organic conducting polymer sensors.

10. The method of claim 7 wherein said sensors sense odor by a change in resistance responsive to exposure to said odor.

11. The method of claim 1 wherein said exposing of an array comprises disposing a plurality of different types of sensors in an array.

12. The method of claim 11 wherein said disposing step further comprises selecting at least one type of sensor from the group comprising surface acoustic wave devices, tin oxide detectors, conducting organic polymers, dye-impregnated polymer films on fiber optic detectors, polymer-coated micromirrors, quartz crystal microbalances, electrochemical gas detectors, chemically sensitive field-effect transistors, carbon black-polymer composite chemiresistors, micro-electro-mechanical system devices, and micro-opto-electro-mechanical system devices.

13. The method of claim 12 wherein at least one type of sensor comprises carbon black-polymer composite sensors.

14. The method of claim 12 wherein at least one type of sensor comprises tin oxide sensors.

15. The method of claim 14 wherein at least one type of sensor comprises bulk organic conducting polymer sensors.

16. The method of claim 15 wherein a second type of sensor comprises carbon black-polymer composite sensors.

* * * * *